(12) United States Patent
Ito et al.

(10) Patent No.: US 9,953,407 B2
(45) Date of Patent: Apr. 24, 2018

(54) WAFER INSPECTION METHOD AND WAFER INSPECTION APPARATUS

(71) Applicant: DISCO CORPORATION, Tokyo (JP)

(72) Inventors: Yusaku Ito, Tokyo (JP); Hirohide Yano, Tokyo (JP); Tomoyuki Yaguchi, Tokyo (JP)

(73) Assignee: Disco Corporation, Tokyo (JP)

( * ) Notice: Subject to any disclaimer, the term of this patent is extended or adjusted under 35 U.S.C. 154(b) by 233 days.

(21) Appl. No.: 14/871,177

(22) Filed: Sep. 30, 2015

(65) Prior Publication Data

US 2016/0098828 A1 Apr. 7, 2016

(30) Foreign Application Priority Data

Oct. 6, 2014 (JP) .................................. 2014-205552

(51) Int. Cl.
*G06T 7/00* (2017.01)
*G01N 21/95* (2006.01)

(52) U.S. Cl.
CPC ....... *G06T 7/0004* (2013.01); *G01N 21/9501* (2013.01); *G06T 2207/30148* (2013.01)

(58) Field of Classification Search
CPC .......... G06T 7/04; G01N 21/86; G01N 21/95; H04N 19/80
See application file for complete search history.

(56) References Cited

U.S. PATENT DOCUMENTS

| 8,577,180 B2* | 11/2013 | Azuma | H04N 19/80 |
| | | | 283/100 |
| 2001/0030296 A1* | 10/2001 | Ishimaru | G01N 21/474 |
| | | | 250/559.4 |
| 2013/0155400 A1* | 6/2013 | Nakao | G01N 21/9501 |
| | | | 356/237.2 |

FOREIGN PATENT DOCUMENTS

JP 2005-153090 6/2005

* cited by examiner

*Primary Examiner* — Sathyanaraya V Perungavoor
*Assistant Examiner* — Patricia I Young
(74) *Attorney, Agent, or Firm* — Greer Burns & Crain Ltd.

(57) ABSTRACT

A wafer inspection method includes a step of picking up an image of a processed face of a wafer, a step of extracting a pixel having a pixel value higher than those of peripheral pixels as a characteristic point from among pixels in each predetermined region of picked up image data to create a first image, and a step of extracting a pixel having a pixel value lower than those of peripheral pixels as a characteristic point from among the pixels in each predetermined region of the picked up image data to create a second image. The first and second images are used to inspect the processed face of the wafer.

1 Claim, 5 Drawing Sheets

WAFER INSPECTION METHOD AND WAFER INSPECTION APPARATUS

BACKGROUND OF THE INVENTION

Field of the Invention

The present invention relates to a wafer inspection method and a wafer inspection apparatus for inspecting a polishing failure of a wafer.

Description of the Related Art

In a grinding and polishing apparatus, a polishing process is carried out for a wafer after a grinding process to remove grinding damage remaining on the wafer to enhance the flexural strength of the wafer (refer, for example, to Japanese Patent Laid-Open No. 2005-153090). The grinding and polishing apparatus disclosed in Japanese Patent Laid-Open No. 2005-153090 includes a turntable on which a plurality of chuck tables are disposed, grinding means and polishing means provided around the turntable. The turntable is rotated intermittently to successively position the wafer on the chuck table to the grinding means and the polishing means. Therefore, the grinding process and the polishing process are carried out successively for the wafer without removing the wafer from the chuck table.

SUMMARY OF THE INVENTION

Incidentally, when a polishing process is carried out by dry polishing or the like, grinding marks marked upon grinding processing of a wafer cannot sometimes be removed sufficiently, and radial undulations are sometimes caused by grinding marks remaining on the processed face of the wafer. As polishing failures of a wafer, scratches, cracks, fine particles and so forth sometimes occur in addition to grinding marks. Although such polishing failures are visually confirmed by an operator, since almost all wafers are normal and it is difficult to visually confirm grinding marks, scratches and so forth on a processed face of a wafer, the inspection itself is cumbersome.

Therefore, also it is investigated to pick up an image of a processed face of a wafer by an optical system and inspect a polishing failure on the basis of the picked up image. However, in order to inspect a large-diameter wafer such as a 12-inch wafer by a single time inspection operation, the picked up image must be produced from a large amount of picked up image data. Therefore, a memory of a large capacity is required and a long period of time is required for processing of the image. Further, if polishing failures such as grinding scars, scratches, cracks and fine particles exist in a mixed manner on a processed face of a wafer, the polishing failures existing on the processed face interfere with each other to make it difficult to inspect the polishing failures from a picked up image.

In particular, although it is difficult to process a large amount of image data, characteristics of a polishing failure cannot be extracted by simple sampling out of data for reducing the data amount. Further, polishing failures including grinding marks and cracks which have different characteristics from each other exist in a mixed manner, and it is difficult to inspect polishing failures of the different characteristics by a single time image pickup (single time measurement) to detect all failures.

Therefore, it is an object of the present invention to provide a wafer inspection method and a wafer inspection apparatus by which polishing failures on a processed face of a wafer can be inspected in a short period of time with a high degree of accuracy.

In accordance with an aspect of the present invention, there is provided a wafer inspection method for inspecting a processed face of a wafer processed by grinding and polishing, including an image pickup step of picking up an image of the processed face of a wafer held on a chuck table, and a first image creation step of delimiting picked up image data obtained by the image pickup at the image pickup step for each predetermined region and extracting a pixel having a pixel value higher than those of peripheral pixels as a characteristic point in the predetermined region to create a first image.

According to the configuration described above, only a pixel having a pixel value higher than those of peripheral pixels is extracted as a characteristic point for each predetermined region of picked up image data to create a first picked up image. At this time, scratches, cracks and fine particles are represented by pixels having comparatively high pixel values while grinding marks are represented by pixels having comparatively low pixel values. Since the first picked up image is created only from the pixels of the picked up data having high pixel values, no grinding mark is displayed on the first picked up image. Therefore, the presence of scratches and so forth can be inspected with a high degree of accuracy from the first picked up image from which the grinding marks are removed. Further, since the first image is created only from part of the picked up image data, the processing time period required for image creation can be reduced. It is to be noted that the picked up image data signifies data on which creation of an image is based.

In accordance with another aspect of the present invention, there is provided a wafer inspection method for inspecting a processed face of a wafer processed by grinding and polishing, including an image pickup step of picking up an image of the processed face of a wafer held on a chuck table, and a second image creation step of delimiting picked up image data obtained by the image pickup at the image pickup step for each predetermined region and extracting a pixel having a pixel value lower than those of peripheral pixels as a characteristic point in the predetermined region to create a second image.

According to the configuration described above, only a pixel having a pixel value lower than those of peripheral pixels is extracted as a characteristic point for each predetermined region of picked up image data to create a second picked up image. At this time, scratches, cracks and fine particles are represented by pixels having comparatively high pixel values while grinding marks are represented by pixels having comparatively low pixel values. Since the second picked up image is created only from the pixels of the picked up data having low pixel values, scratches and so forth are not displayed on the second picked up image. Therefore, presence of grinding marks can be inspected with a high degree of accuracy from the second picked up image from which the scratches and so forth are removed. Further, since the second image is created only from part of the picked up image data, the processing time period required for image creation can be reduced.

In accordance with a further aspect of the present invention, there is provided a wafer inspection method for inspecting a processed face of a wafer processed by grinding and polishing, including an image pickup step of picking up an image of the processed face of a wafer held on a chuck table, a first image creation step of delimiting picked up image data obtained by the image pickup at the image pickup step for each predetermined region and extracting a pixel having a pixel value higher than those of peripheral pixels as a characteristic point in the predetermined region to create a first image, and a second image creation step of extracting a pixel having a pixel value lower than those of peripheral pixels as a characteristic point in the predetermined region to create a second image.

According to the configuration described above, only a pixel having a pixel value higher than those of peripheral pixels is extracted as a characteristic point for each predetermined region of picked up image data to create a first picked up image, and only a pixel having a pixel value lower than those of peripheral pixels is extracted as a characteristic point for each predetermined region of the picked up image data to create a second picked up image. Since grinding marks are not displayed on the first picked up image as described herein above, the presence of scratches and so forth can be inspected with a high degree accuracy. Further, since scratches and so forth are not displayed on the second picked up image, the presence of grinding marks can be inspected with a high degree accuracy. Further, since the first and second images are created only from part of the picked up image data, the processing time period required for image creation can be reduced.

In accordance with a still further aspect of the present invention, there is provided a wafer inspection apparatus for inspecting a processed face of a wafer processed by grinding and polishing, including a chuck table configured to hold a wafer thereon, image pickup means for picking up an image of the processed face of the wafer held by the chuck table, a first image creation unit configured to delimit picked up image data obtained by the image pickup by the image pickup means for each predetermined region and extract a pixel having a pixel value higher than those of peripheral pixels in the predetermined region to create a first image, a second image creation unit configured to extract a pixel having a pixel value lower than those of peripheral pixels in the predetermined region to create a second image, and a selection unit configured to select one of the first image creation unit and the second image creation unit in response to an inspection target.

Preferably, the wafer inspection apparatus is configured such that the image pickup means is configured from a line sensor having a linear image pickup range of a predetermined length in a radial direction of the wafer; the wafer inspection apparatus further includes rotation means for rotating the chuck table and the image pickup means relative to each other around the center of the wafer, and horizontally moving means for moving the chuck table and the image pickup means relative to each other in a diametrical direction of the wafer; and every time an image of the wafer is picked up by the image pickup means while the wafer is rotated by 360 degrees by the rotation means, the image pickup means is moved in a diametrical direction of the wafer by a distance corresponding to a length of the image pickup range by the horizontally moving means and then the pieces of picked up image data obtained by the image pickup of an overall area of the processed face are used to inspect the processed face of the wafer.

The above and other objects, features and advantages of the present invention and the manner of realizing them will become more apparent, and the invention itself will best be understood, from a study of the following description and appended claims with reference to the attached drawings showing a preferred embodiment of the invention.

DETAILED DESCRIPTION OF THE PREFERRED EMBODIMENT

Figure 1:
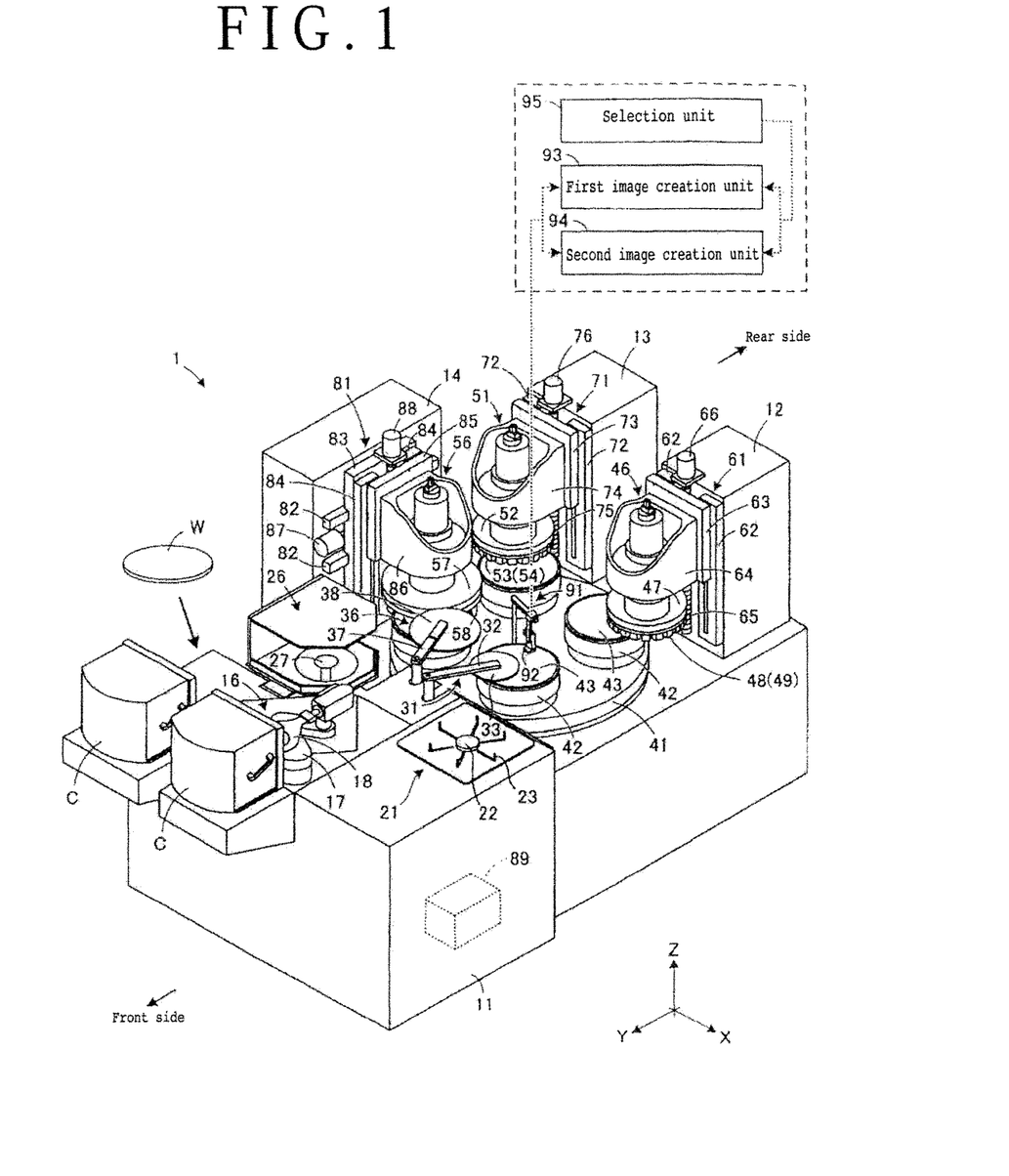
FIG. 1 is a perspective view of a grinding and polishing apparatus according to an embodiment.

In the following, a grinding and polishing apparatus according to an embodiment is described with reference to the accompanying drawings. FIG. 1 is a perspective view of the grinding and polishing apparatus according to the present embodiment. It is to be noted that the present embodiment is not limited to the configuration depicted in FIG. 1. The grinding and polishing apparatus may be configured in any manner only if it can carry out a grinding process and a polishing process for a wafer.

As depicted in FIG. 1, the grinding and polishing apparatus 1 is a processing apparatus of the full automatic type and is configured so as to fully automatically carry out a series of processes for a wafer W including a carrying-in process, a rough grinding process, a finish grinding process, a polishing process, a washing process and a carrying-out process. The wafer W is formed in a substantially disk shape and is carried in a state in which it is accommodated in a cassette C into the grinding and polishing apparatus 1. It is to be noted that the wafer W may be any plate-shaped work which can be made a grinding target and a polishing target and may be a semiconductor substrate of silicon, gallium arsenide or the like, or may be an inorganic material substrate of ceramic, glass, sapphire or the like, or else may be a package substrate of a semiconductor product or the like.

On the front side of a base 11 of the grinding and polishing apparatus 1, a pair of cassettes C in each of which a plurality of wafers W are accommodated are placed. On the rear of the pair of cassettes C, a cassette robot 16 is provided which loads and unloads a wafer W into and from the cassettes C. On both oblique rear sides of the cassette robot 16, a positioning mechanism 21 for positioning a wafer W before processing and a washing mechanism 26 for washing a wafer W after processing are provided. Between the positioning mechanism 21 and the washing mechanism 26, carrying-in means 31 for carrying in a wafer W before processing to a chuck table 42 and carrying-out means 36 for carrying out a wafer W after processing from the chuck table 42.

The cassette robot 16 is configured from a hand unit 18 provided at a tip end of a robot arm 17 configured from a multi-node link. By the cassette robot 16, a wafer W before processing is transported from a cassette C to the positioning mechanism 21, and a wafer W after processing is transported from the washing mechanism 26 to a cassette C. The positioning mechanism 21 is configured from a plurality of positioning pins 23 disposed around a temporary placement table 22 for movement toward and away from the center of the temporary placement table 22. In the positioning mechanism 21, the plurality of positioning pins 23 are abutted with an outer circumferential edge of a wafer W placed on the temporary placement table 22 to position the center of the wafer W at the center of the temporary placement table 22.

The carrying-in means 31 is configured from a carrying-in pad 33 provided at a tip end of a carrying-in arm 32 which can be pivoted on the base 11. In the carrying-in means 31, a wafer W is lifted from the temporary placement table 22 by the carrying-in pad 33 and the carrying-in pad 33 is turned by the carrying-in arm 32 to carry the wafer W onto the chuck table 42. The carrying-out means 36 is configured from a carrying-out pad 38 provided at a tip end of a carrying-out arm 37 which can be pivoted on the base 11. In the carrying-out means 36, a wafer W is lifted from the chuck table 42 by the carrying-out pad 38 and the carrying-out pad 38 is turned by the carrying-out arm 37 to carry out the wafer W from the chuck table 42.

Figure 3A:
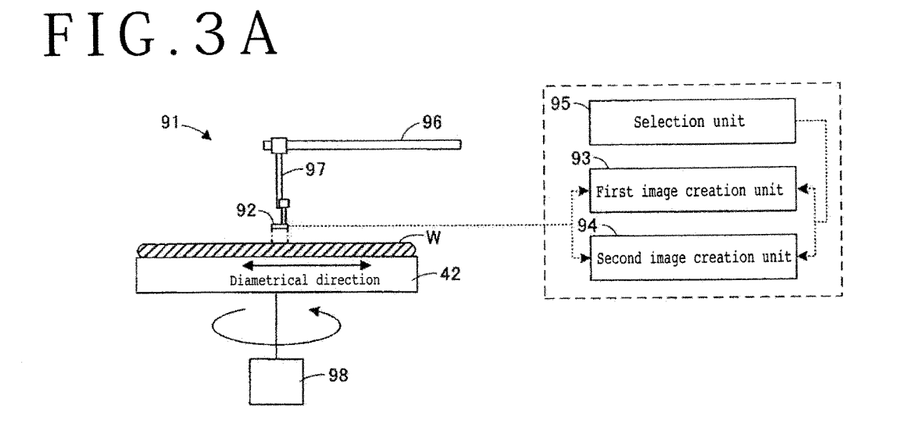
FIGS. 3A and 3B are explanatory views of an image pickup step by a wafer inspection apparatus according to the present embodiment.

The washing mechanism 26 is configured from various nozzles (not depicted) which inject washing water and dry air toward a spinner table 27. By the washing mechanism 26, the spinner table 27 which holds a wafer W thereon is moved down into the base 11, and washing water is injected in the base 11 to spinner-wash the wafer W, whereafter dry air is injected to dry the wafer W. Behind the carrying-in means 31 and the carrying-out means 36, a turntable 41 is provided and has four chuck tables 42 disposed thereon in an equidistantly spaced relationship from each other in a circumferential direction. On an upper face of each chuck table 42, a holding face 43 for holding a lower face of a wafer W is formed. Further, each chuck table 42 is configured for rotation by rotation means 98 (refer to FIG. 3) provided on the base 11.

When the turntable 41 rotates intermittently at intervals of 90 degrees, a wafer W is positioned successively to a carrying-in and carrying-out position at which the wafer W is carried in and out, respectively, a rough grinding position at which the wafer W confronts with rough grinding means 46, a finish grinding position at which the wafer W confronts with finish grinding means 51, and a polishing position at which the wafer confronts with polishing means 56. At the rough grinding position, the wafer W is roughly ground to a predetermined thickness by the rough grinding means 46. At the finish grinding position, the wafer W is finish ground to a finish thickness by the finish grinding means 51. At the polishing position, the wafer W is polished by the polishing means 56. Around the turntable 41, columns 12, 13 and 14 are provided uprightly.

On the column 12, moving means 61 is provided which moves the rough grinding means 46 upwardly and downwardly. The moving means 61 includes a pair of guide rails 62 disposed in parallel to the Z axis direction on the front face of the column 12 and a motor-driven Z-axis table 63 provided for sliding movement on the pair of guide rails 62. The rough grinding means 46 is supported on the front face of the Z-axis table 63 through a housing 64. A ball screw 65 is screwed on the rear face side of the Z-axis table 63, and a driving motor 66 is connected to one end of the ball screw 65. When the ball screw 65 is driven to rotate by the driving motor 66, the rough grinding means 46 is moved in the Z axis direction by the guide rails 62.

Similarly, moving means 71 is provided on the column 13 and moves the finish grinding means 51 upwardly and downwardly. The moving means 71 is configured from a pair of guide rails 72 disposed on the front face of the column 13 in parallel to the Z axis direction and a motor-driven Z-axis table 73 provided for sliding movement on the pair of guide rails 72. The finish grinding means 51 is supported on the front face of the Z-axis table 73 through a housing 74. A ball screw 75 is screwed on the rear face side of the Z-axis table 73, and a driving motor 76 is connected to one end of the ball screw 75. When the ball screw 75 is driven to rotate by the driving motor 76, the finish grinding means 51 is moved in the Z-axis direction along the guide rails 72.

The rough grinding means 46 and the finish grinding means 51 are configured by including mounts 47 and 52 at a lower end of cylindrical spindles. On a lower face of the mount 47 of the rough grinding means 46, a grinding wheel 49 for rough grinding is mounted. The grinding wheel 49 has a plurality of rough grindstones 48 disposed annularly thereon. Each rough grindstone 48 is configured from a diamond grindstone including diamond abrasive grain solidified by a binding agent such as, for example, metal bond or resin bond. Meanwhile, a grinding wheel 54 is mounted on a lower face of the mount 52 of the finish grinding means 51 and has a plurality of finish grindstones 53 disposed annularly thereon. Each finish grindstone 53 is formed from grindstone grain of a particle size smaller than that of the rough grindstone 48. By the rough grinding process and the finish grinding process, the wafer W is thinned to a predetermined thickness.

On the column 14, moving means 81 is provided and positions the polishing means 56 with respect to the wafer W at a predetermined polishing position. The moving means 81 includes a pair of guide rails 82 disposed on the front face of the column 14 in parallel to the Y axis direction and a motor-driven Y-axis table 83 provided for sliding movement on the pair of guide rails 82. The moving means 81 further includes a pair of guide rails 84 disposed on the front face of the Y-axis table 83 in parallel to the Z axis direction and a motor-driven Z-axis table 85 provided for sliding movement on the pair of guide rails 84. The polishing means 56 is supported on the front face of the Z-axis table 85 through a housing 86.

A ball screw (not depicted) is screwed on the rear face side of the Y-axis table 83 and the Z-axis table 85, and driving motors 87 and 88 are connected to one end of the ball screw. When the ball screw is driven to rotate by the driving motors 87 and 88 and the polishing means 56 is moved in the Y-axis direction and the Z-axis direction along the guide rails 82 and 84. The polishing means 56 is configured by providing a mount 57 at a lower end of a cylindrical spindle. A polishing pad 58 is mounted on a lower face of the mount 57. The polishing pad 58 is formed from a foamed material, a fibrous material or the like. In a polishing process, an upper face of a wafer W is polished a little to remove grinding damages remaining on the wafer W after a rough grinding process and a finish grinding process.

In this case, arcuate grinding marks are traced out on the processed face of the wafer W as grinding damage after the rough grinding process and the finish grinding process. Although the processed face of the wafer W is polished by the polishing process, if the difference in height of a grinding mark is great, then the grinding mark remains as a grinding mark (radial undulation) S1 on the wafer W (refer to FIG. 2). If this polishing failure is confirmed visually from the outside of the apparatus by an operator, then this makes a big burden on the operator. Therefore, in the present embodiment, a wafer inspection apparatus 91 for inspecting the processed face of a wafer W is provided at the carrying-in and carrying-out position such that an image of the processed face of the wafer W after the polishing process is picked up to inspect polishing failures.

Figure 2:
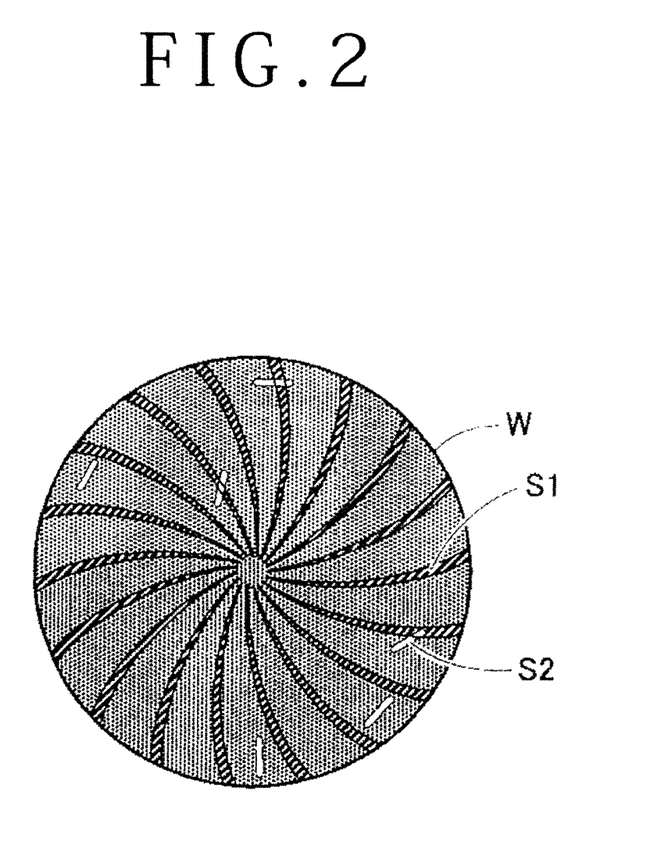
FIG. 2 is a view depicting a state of a processed face of a wafer according to the present embodiment.

Incidentally, as depicted in FIG. 2, such polishing failures as scratches, cracks and fine particles (hereinafter referred to as scratches S2 and so forth) exist on the processed face of a wafer W in addition to the grinding marks S1 described above, and it is difficult to visually inspect the wafer W on which such various polishing failures as described above exist in a mixed manner. Further, in order to capture polishing failures on the processed face of a wafer W by the wafer inspection apparatus 91, image pickup means 92 (refer to FIG. 1) having a high resolution must be used. As the resolution of the image pickup means 92 increases, a memory of an increased capacity must be prepared in order to create an image from image data of the overall area of the wafer W, which further increases the processing time period required for image creation. It is to be noted that the picked up image data signifies data on which creation of an image is based, and individual pieces of data are associated with pixels of the image.

The inventor of the present invention has paid attention to the fact that the scratches S2 and so forth are represented by comparatively high pixel values while the grinding marks S1 are represented by comparatively low pixel values to make the present invention. The gist of the present invention resides in that some bright data elements and some dark data elements included in picked up image data of the overall area of the wafer W are extracted as characteristic points to create two different images including an image which includes only comparatively bright characteristic points and another image which includes only comparatively dark characteristic points (refer to FIGS. 4B and 4C). Consequently, the scratches S2 and so forth can be inspected on the image which includes only comparatively bright characteristic points, and the grinding marks S1 can be inspected on the image which includes only comparatively dark characteristic points. Further, since only it is necessary to create an image of a low resolution from part of data elements of picked up image data, the capacity of the memory can be suppressed and the processing time required for image creation can be reduced.

Referring back to FIG. 1, the wafer inspection apparatus 91 is configured such that it irradiates light upon the wafer W from above and an image of the processed face of the wafer W on the chuck table 42 is picked up from above by the image pickup means 92. Since the scratches S2 (refer to FIG. 2) and so forth are formed from steep irregularities on the processed face of the wafer W, upon image pickup, the light is scattered strongly by the irregularities and the scattered light comes to the image pickup means 92 and is represented by pixels of comparatively high pixel values on the picked up image. Meanwhile, since the grinding marks S1 (FIG. 2) are each formed from a moderate slope on the processed face of the wafer W, upon image pickup, scattered light little comes to the image pickup means 92 and is represented by pixels of comparatively low pixel values on the picked up image.

The wafer inspection apparatus 91 includes a first image creation unit 93 which creates a first image (refer to FIG. 4B) formed from pixels of comparatively high pixel values for the inspection of the scratches S2 and so forth, and a second image creation unit 94 which creates a second image (refer to FIG. 4C) formed from pixels of comparatively low pixel values for the inspection of the grinding marks S1. The wafer inspection apparatus 91 further includes a selection unit 95 for selecting one of the first and second image creation units 93 and 94 in response to an inspection target as in a case in which the scratches S2 and so forth are inspected and another case in which the grinding marks S1 are inspected. It is to be noted that details of a first image creation step by the first image creation unit 93 and a second image creation step by the second image creation unit 94 are hereinafter described.

The grinding and polishing apparatus 1 includes control means 89 for integrally controlling the components thereof. The control means 89 carries out various controls of a rough grinding step by the rough grinding means 46, a finish grinding step by the finish grinding means 51, a polishing process by the polishing means 56, an image pickup step by the image pickup means 92 and so forth. It is to be noted that the control means 89, first image creation unit 93, second image creation unit 94 and selection unit 95 are configured from a processor which executes various processes, a memory and so forth. The memory is configured from one or a plurality of storage media such as a read only memory (ROM), a random access memory (RAM) and the like.

In such a grinding and polishing apparatus 1 as described above, a wafer W is transported from within a cassette C to the positioning mechanism 21 and is centered by the positioning mechanism 21. Then, the wafer W is carried in to the chuck table 42 and is successively positioned at the rough grinding position, finish grinding position and polishing position by rotation of the turntable 41. At the rough grinding position, the wafer W undergoes a rough grinding process; at the finish grinding position, the wafer W undergoes a finish grinding process; and at the polishing position, the wafer W undergoes a polishing process. Then, polishing failures of the wafer W after the polishing are inspected, whereafter the wafer W is washed by the washing mechanism 26 and then carried out from the washing mechanism 26 to the cassette C.

Figure 3B:
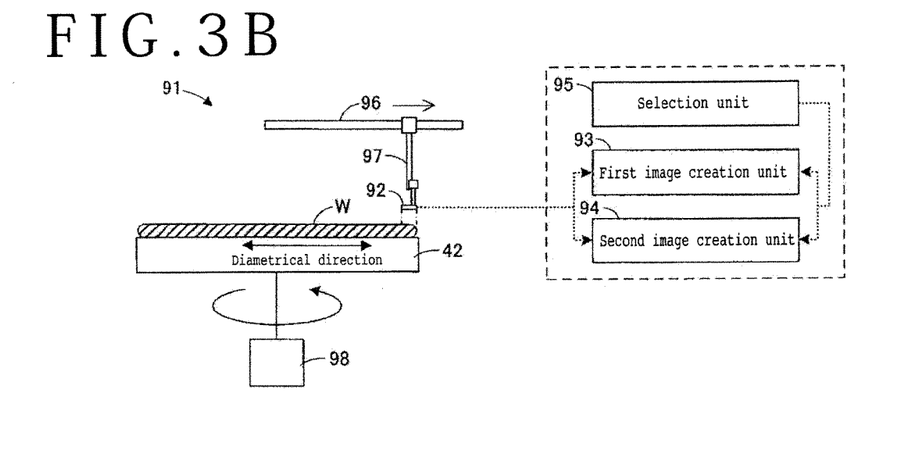

In the following, an image pickup operation by the wafer inspection apparatus is described. FIGS. 3A and 3B are explanatory views of the image pickup step by the wafer inspection apparatus according to the present embodiment. FIGS. 4A to 4D are explanatory views of first and second image creation steps by the wafer inspection apparatus according to the present embodiment. FIGS. 5A and 5B are photographs depicting first and second images according to the present embodiment. It is to be noted that the image pickup step of the wafer inspection apparatus depicted in FIGS. 3A and 3B is a mere example, and an image of the processed face of a wafer may be picked up by any operation only if an image of the processed face of the wafer can be picked up by the operation.

As depicted in FIG. 3A, the image pickup means 92 of the wafer inspection apparatus 91 is a line sensor which has a linear image pickup range of a predetermined length (for example, 1,024 pixels) in a radial direction of the wafer W and provides pixel values of 12-bit gradations. The image pickup means 92 is positioned above the chuck table 42 by horizontally moving means 96 and upwardly and downwardly moving means 97. The horizontally moving means 96 extends such that it moves the chuck table 42 and the image pickup means 92 relative to each other in a diametrical direction of the wafer W, and the image pickup means 92 is mounted for horizontal movement on the horizontally moving means 96 through the upwardly and downwardly moving means 97. The upwardly and downwardly moving means 97 extends such that it moves the wafer W and the image pickup means 92 toward and away from each other, and the image pickup means 92 is mounted for up and down movement on the upwardly and downwardly moving means 97.

On the chuck table 42, a wafer W is held such that the center of the wafer W is aligned with the center of the chuck table 42. At a lower portion of the chuck table 42, the rotation means 98 is provided which rotates the chuck table 42 and the image pickup means 92 relative to each other around the center of the wafer W. At the image pickup step of the wafer inspection apparatus 91 configured in such a manner as described above, the linear image pickup range of the image pickup means 92 is positioned at the position of the center of the wafer W, and while an image of the wafer W is picked up by the image pickup means 92, the chuck table 42 is rotated by the rotation means 98. Consequently, an image of the processed face of the wafer W is picked up over 360 degrees, and pieces of picked up image data are fetched into the first and second image creation units 93 and 94.

Then, every time an image of the wafer W is picked up over 360 degrees by the image pickup means 92, the image pickup means 92 is moved to the outer side in the diametrical direction by a distance equal to the length of the linear image pickup range by the horizontally moving means 96 as depicted in FIG. 3B. As this image pickup operation is carried out repetitively, pieces of picked up image data representing the overall area of the processed face of the wafer W are fetched into the first and second image creation units 93 and 94. It is to be noted that, while the wafer inspection apparatus in the present embodiment is configured such that images are successively picked up while the image pickup range is successively displaced from the center of the processed face of the wafer W to the outer side in the diametrical direction, it may be configured otherwise such that images are successively picked up while the image pickup range is successively displaced toward the inner side in the diametrical direction from the outer periphery side of the processed face of the wafer W.

Figure 4A:
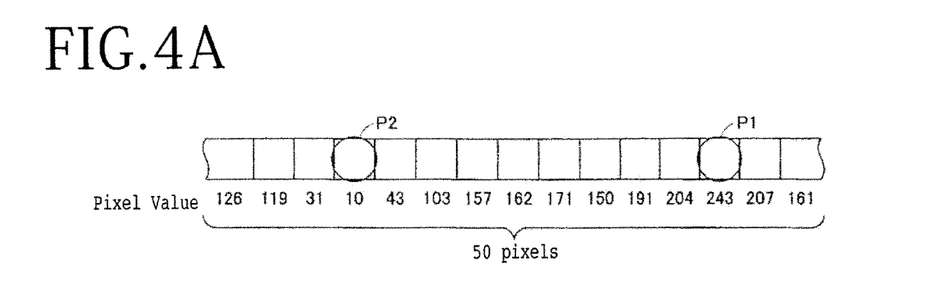
FIGS. 4A to 4D are explanatory views of first and second image production steps by the wafer inspection apparatus according to the present embodiment.
Figure 5A:
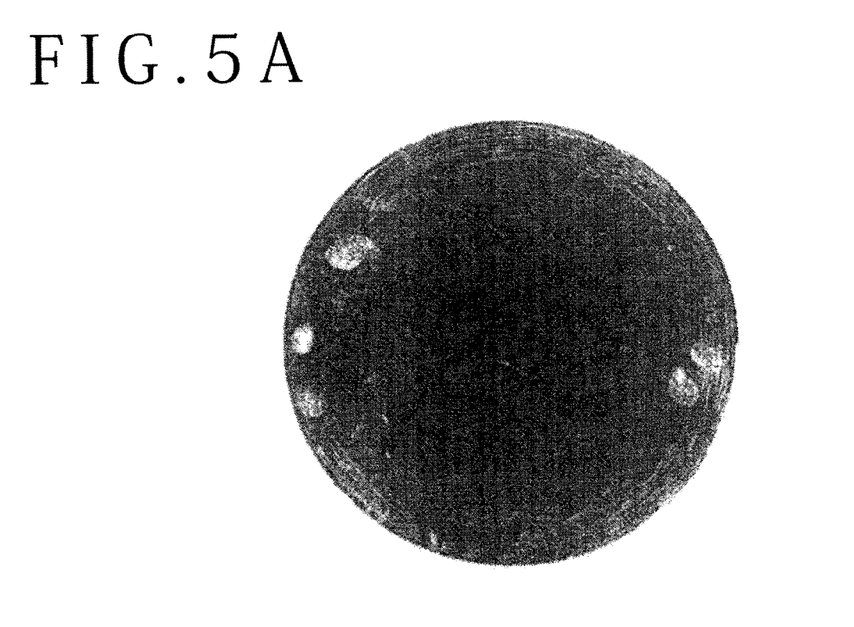
FIGS. 5A and 5B are photographs depicting first and second images according to the present embodiment.
Figure 5B:
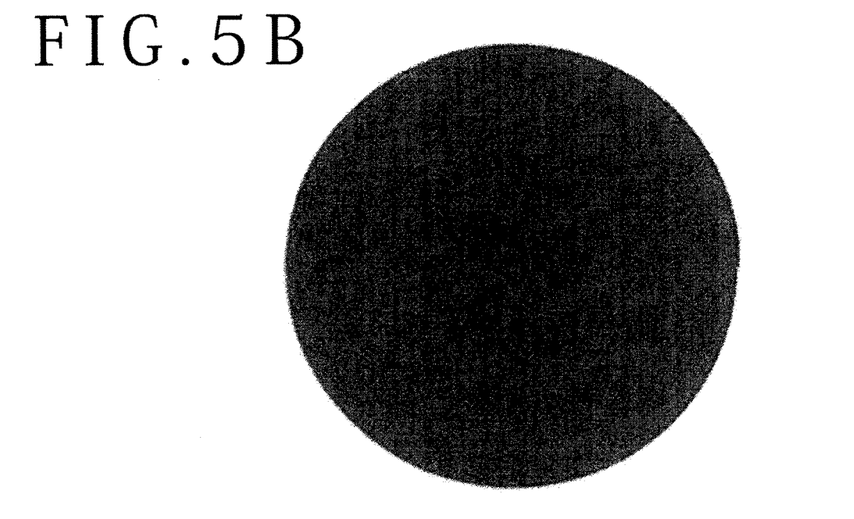

As depicted in FIG. 4A, the pieces of picked up image data fetched in the first image creation unit 93 (refer to FIG. 3A) are delimited for each predetermined region (for example, 50 pixels), and a pixel having the highest pixel value (for example, the highest luminance value among pixel values in a range of 4 to 12 bits) in the predetermined range is extracted as a characteristic point. In this case, the pixel having the highest pixel value (for example, a pixel value 243) among the 50 pixels of the predetermined region is extracted as a characteristic point P1. Similarly, the pieces of picked up image data fetched in the second image creation unit (refer to FIG. 3A) are delimited for each predetermined region (for example, 50 pixels), and a pixel value having the lowest pixel value (for example, the lowest luminance value among pixel values in a range of 0 to 8 bits) in the predetermined range is extracted as a characteristic point P2. In this case, the pixel having the lowest pixel value (for example, a pixel value 10) among the 50 pixels of the predetermined region is extracted as a characteristic point P2.

Figures 4B, 4C:
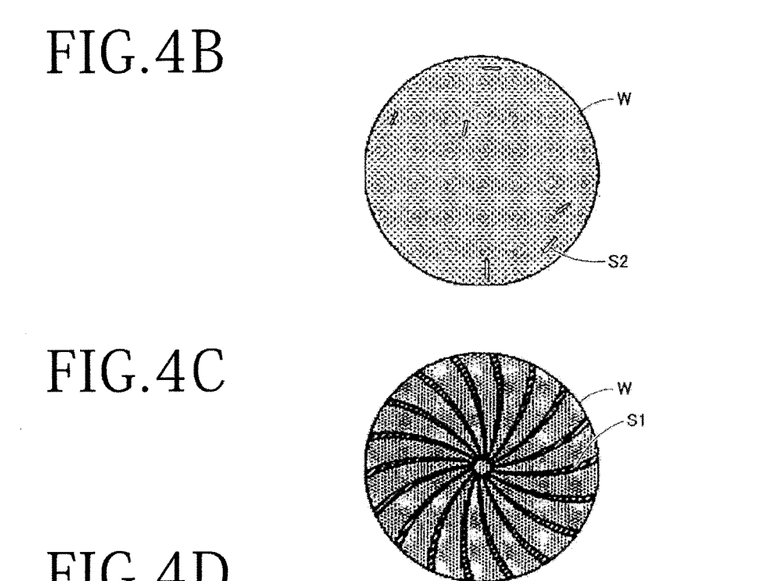

As depicted in a schematic view of FIG. 4B and a photograph of FIG. 5A, at the first image creation step by the first image creation unit 93 (refer to FIG. 3A), only a pixel having a high pixel value is extracted for each predetermined region from among all pieces of picked up image data and used to create a first image. In this case, although the picture quality is degraded because the total pixel number of the first image is small, since the amount of data used for image creation is small, the processing time period is reduced. Further, since the first image is created only from pixels having comparatively high pixel values, a polishing failure by a scratch S2 is emphasized in the image.

As depicted in the schematic view of FIG. 4C and the photograph of FIG. 5B, at the second image creation step by the second image creation unit 94 (refer to FIG. 3A), only pixels extracted for each predetermined region and having low pixel values are used from among all pieces of picked up image data to create a second image. In this instance, although the picture quality is degraded because the total pixel number of the second image is small, since the amount of data used for image creation is small, the processing time period is reduced. Further, since the second image is created only from pixels having comparatively low pixel values, a polishing failure by a grinding mark S1 is emphasized in the image.

In this manner, the image pickup means 92 (refer to FIG. 3A) having a high resolution is used to acquire picked up image data in an overall processed face of a wafer W to eliminate missing (loss of image pickup) of fine polishing failures existing on the processed face and sample out unnecessary data from a large amount of picked up image data to create an image of low picture quality. Consequently, first and second images which include no missing pixels indicative of polishing failures such as the scratches S2, the grinding marks S1 and so forth are created from a small amount of data. Even with the first and second images created in low picture quality, it is possible to inspect polishing failures favorably because polishing failures such as the scratches S2, the grinding marks S1 and so forth are included in the first and second images with certainty.

Further, the selection unit 95 (refer to FIG. 3A) selects one of the first and second image creation units 93 and 94 in response to an inspection target as in a case in which the scratches S2 and so forth are inspected or another case in which the grinding marks S1 are inspected. After one of the first and second image creation units 93 and 94 is selected by the selection unit 95, a first image or a second image is created by the selected image creation unit and is selectively displayed on a display apparatus not depicted. By displaying only a desired image on the display apparatus in response to an inspection target selected by the operator in this manner, it is possible to inspect the scratches S2 and so forth and the grinding marks S1 distinctly from each other.

Figure 4D:
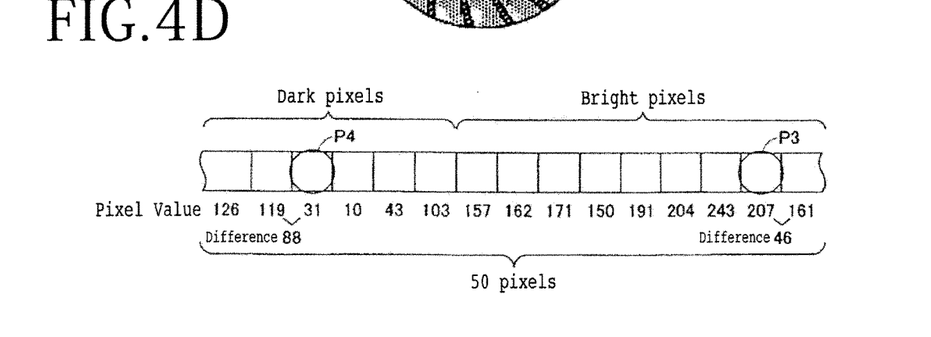

It is to be noted that, while the first image creation unit 93 is configured such that a pixel having the highest pixel value is extracted as a characteristic point to create a first image, the first image creation unit 93 is not limited to this configuration. The first image creation unit 93 may delimit picked up image data for each predetermined region and extract a pixel having a higher pixel value than those of peripheral pixels in the predetermined region as a characteristic point to create a first image. For example, a pixel having a higher pixel value which exhibits the greatest difference from an adjacent pixel (pixel value) may be extracted as a characteristic point as depicted in FIG. 4D. In this case, a difference between each pixel having a high pixel value (pixel value of 128 or more) and another pixel adjacent to the pixel having the high pixel value is calculated and the pixel (pixel value 207≥128) of the high pixel value which indicates a maximum difference (for example, a difference 46) is extracted as a characteristic point P3.

Similarly, while the second image creation unit 94 is configured such that a pixel having the lowest pixel value is extracted as a characteristic point to create a second image, the second image creation unit 94 is not limited to this configuration. The second image creation unit 94 may delimit picked up image data for each predetermined region and extract a pixel having a lower pixel value than those of peripheral pixels in the predetermined region as a characteristic point to create a second image. For example, a pixel having a lower pixel value which exhibits the greatest difference from an adjacent pixel (pixel value) may be extracted as a characteristic point as depicted in FIG. 4D. In this case, a difference between each pixel having a low pixel value (pixel value of 127 or less) and another pixel adjacent to the pixel having the low pixel value is calculated and the pixel (pixel value 31≤127) of the low pixel value which indicates a maximum difference (for example, a difference 88) is extracted as a characteristic point P4.

It is to be noted that, in the inspection of polishing failures, the operator may visually observe first and second images to make a decision or the wafer inspection apparatus 91 may make a decision automatically. Where polishing failures are to be decided by the wafer inspection apparatus 91, the wafer inspection apparatus 91 may be configured such that it automatically decides polishing failures from the magnitude of pixel values of scratches and so forth indicating polishing failures or the ratio of pixels indicating polishing failures. Further, the wafer inspection apparatus 91 may be configured such that it stores positions of polishing failures on a processed face of a wafer W and utilized for processing at a later stage.

As described above, in the wafer inspection apparatus 91 according to the present embodiment, only a pixel having a higher pixel value than those of peripheral pixels is extracted as a characteristic point for each predetermined region of image pickup data to create a first picked up image while only a pixel having a lower pixel value than those of peripheral pixels is extracted as a characteristic point for each predetermined region of image pickup data to create a second picked up image. Since grinding marks (radial undulations) S1 are not displayed in the first picked up image, presence of scratches S2 and so forth can be inspected with a high degree of accuracy. Further, since the scratches S2 and so forth are not displayed in the second picked up image, presence of grinding marks S1 can be inspected with a high degree of accuracy. Further, since the first and second images are created from part of the picked up image data, the processing time period required for image creation can be reduced.

It is to be noted that the present invention is not limited to the embodiment described above and can be carried out in various modified forms. In the embodiment described above, the size, shape and so forth depicted in the accompanying drawings are not limited to them and can be suitably changed without departing from a scope within which the effects of the present invention are achieved. Further, the present invention can be carried out in suitable alterations without departing from the scope of the object of the present invention.

For example, while, in the embodiment described above, the wafer inspection apparatus 91 is configured so as to carry out the first image creation step and the second image creation step, the wafer inspection apparatus 91 is not limited to this configuration. The wafer inspection apparatus 91 may be configured so as to carry out at least one of the first image creation step and the second image creation step. Further, while, in the embodiment described above, the wafer inspection apparatus 91 is configured such that it inspects a processed face of a wafer after polishing, the wafer inspection apparatus 91 is not limited to this configuration and may be configured otherwise such that it inspects a processed face of a wafer after grinding.

Further, while, in the embodiment described above, the image pickup means 92 is configured from a line sensor, it is not limited to this configuration. Only it is necessary for the image pickup means 92 to be able to pick up an image of a processed face of a wafer W supported on the chuck table 42, and the image pickup means 92 may be configured otherwise from an area sensor which can pick up an image two-dimensionally.

Further, the wafer inspection apparatus 91 in the embodiment described above may be configured such that, if the wafer inspection apparatus 91 decides that a wafer W fails in polishing, then it carries out a polishing process again for the wafer W or it discards the wafer W without carrying out a polishing process again for the wafer W.

Further, while the rotation means 98 in the embodiment described above is configured such that it rotates the chuck table 42 with respect to the image pickup means 92, the rotation means 98 is not limited to this configuration. Only it is necessary for the rotation means 98 to be configured so as to rotate the chuck table 42 and the image pickup means 92 relative to each other, and the rotation means 98 may rotate the image pickup means 92 with respect to the chuck table 42.

Further, while the horizontally moving means 96 in the embodiment described above is configured such that it moves the image pickup means 92 in a radial direction of a wafer W with respect to the chuck table 42, the horizontally moving means 96 is not limited to this configuration. Only it is necessary for the horizontally moving means 96 to be configured so as to horizontally move the chuck table 42 and the image pickup means 92 relative to each other, and the horizontally moving means 96 may otherwise move the chuck table 42 in a diametrical direction of a wafer W with respect to the image pickup means 92.

Further, while the wafer inspection apparatus 91 in the embodiment described above is configured so as to be incorporated in the grinding and polishing apparatus 1, the configuration of the wafer inspection apparatus 91 is not limited to this. The wafer inspection apparatus 91 may be configured otherwise as an apparatus for exclusive use for picking up an image of a processed face of a wafer W to carry out inspection.

Further, while the first and second image creation units 93 and 94 in the embodiment described above are configured so as to extract one pixel in each predetermined region as a characteristic point, they may otherwise extract a plurality of pixels in each predetermined region as characteristic points.

As described above, the present invention exhibits an effect that polishing failures of a processed face of a wafer can be inspected with a high degree of accuracy in a short period of time and is particularly useful for a grinding and polishing apparatus of the fully automatic type which carries out a grinding process and a polishing process fully automatically and a wafer inspection method carried out on the grinding and polishing apparatus.

The present invention is not limited to the details of the above described preferred embodiment. The scope of the invention is defined by the appended claims and all changes and modifications as fall within the equivalence of the scope of the claims are therefore to be embraced by the invention.

What is claimed is:

1. A wafer inspection apparatus for inspecting a processed face of a wafer processed by grinding and polishing, comprising:
   a chuck table configured to hold a wafer thereon;
   image pickup means for picking up an image of the processed face of the wafer held by the chuck table;
   a first image creation unit configured to delimit picked up image data obtained by the image pickup by the image pickup means for each predetermined region and extract only pixels having a pixel value higher than those of peripheral pixels as a characteristic point in the predetermined region to create a first image;
   a second image creation unit configured to extract only pixels having a pixel value lower than those of peripheral pixels as a characteristic point in the predetermined region to create a second image; and
a selection unit configured to select one of the first image creation unit and the second image creation unit in response to an inspection target;
wherein the image pickup means is configured from a line sensor having a linear image pickup range of a predetermined length in a radial direction of the wafer;
the wafer inspection apparatus further comprises rotation means for rotating the chuck table and the image pickup means relative to each other around the center of the wafer, and horizontally moving means for moving the chuck table and the image pickup means relative to each other in a diametrical direction of the wafer; and
every time an image of the wafer is picked up by the image pickup means while the wafer is rotated by 360 degrees by the rotation means, the image pickup means is moved in a diametrical direction of the wafer by a distance corresponding to a length of the image pickup range by the horizontally moving means and then the pieces of picked up image data obtained by the image pickup of an overall area of the processed face are used to inspect the processed face of the wafer.

* * * * *